US00PP29994P3

(12) United States Plant Patent
Kerley

(10) Patent No.: US PP29,994 P3
(45) Date of Patent: Dec. 18, 2018

(54) ***CALENDULA* PLANT NAMED 'KERCALSUN'**

(50) Latin Name: *Calendula hybrida*
Varietal Denomination: KERCALSUN

(71) Applicant: Timothy Kerley, Over (GB)

(72) Inventor: Timothy Kerley, Over (GB)

( * ) Notice: Subject to any disclaimer, the term of this patent is extended or adjusted under 35 U.S.C. 154(b) by 33 days.

(21) Appl. No.: 15/530,332

(22) Filed: Dec. 23, 2016

(65) Prior Publication Data

US 2018/0184561 P1 Jun. 28, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Keith O. Robinson
(74) *Attorney, Agent, or Firm* — Cassandra Bright

(57) ABSTRACT

A *Calendula* plant named 'KERCALSUN' is disclosed, characterized by bright yellow fully double flowers composed of only ray florets. Plants have an attractive spreading habit and flower prolifically. The flowering period is exceptionally long, from around early Spring until mid to late Fall. Plants are useful for outdoor ornamental purposes, normally produced as an outdoor garden or container plant.

3 Drawing Sheets

Genus and species: *Calendula hybrida.*
Variety denomination: 'KERCALSUN'.

BACKGROUND OF THE INVENTION

'KERCALSUN' is a product of a breeding and selection program for ornamental *Calendula* varieties to be vegetatively propagated. The new plant of the present invention comprises a new and distinct cultivar of *Calendula* plant.

'KERCALSUN' is a seedling resulting from the crossing of the seed parent, a unpatented proprietary *Calendula hybrida* referred to as '10-33-1' with the pollen parent, an unpatented proprietary *Calendula hybrida* referred to as '08/37/23' conducted in August 2011. The selection of the new variety was made in July 2012, by the inventor at a research greenhouse located in Cambridge, UK.

'KERCALSUN' was first asexually reproduced by softwood stem cuttings at a research greenhouse in Cambridge, UK, August 2012 and has been asexually reproduced over an approximately two-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Cambridge, UK:

1 Continuous flowering from early Spring until late Fall.
2. Prolific flowering.
3. Spreading plant habit.
4. Sterile flowers do not set seed, increasing the floriferousness of plants.
5. Bright yellow fully double flowers composed of only ray florets.
6. Good resistance to powdery mildew.

COMPARISON WITH PARENT VARIETIES

Plants of the new cultivar 'KERCALSUN' are similar to plants of the seed parent and plants of the pollen parent in most horticultural characteristics. However, plants of the new cultivar differ in the following:

1. Both parent varieties have single flowers, the new variety has double flowers.

COMPARISON WITH COMMERCIAL CULTIVAR

'KERCALSUN' can be compared to the commercial variety 'Winter Creepers Sun and Flurries', unpatented. However, 'KERCALSUN' differs in the following:

1. Flowers of the new variety are smaller
2. The new variety flowers more abundantly.
3. The new variety produces more branches per plant.
4. The new variety has less ray florets per plant.
5. The new variety has smaller leaves.
6. The new variety rarely produces seed, whereas the comparator regularly produces seed.

'KERCALSUN' can be compared to the commercial variety 'Cheers Yellow', unpatented. However, 'KERCALSUN' differs in the following:

1. Flowers of the new variety are larger.
2. Flowers of the new variety are consistently double, flowers of this comparator become semi-double.
3. The new variety begins flowering later.
4. The new variety has larger leaves.
5. The new variety rarely produces seed, whereas the comparator regularly produces seed.

DESCRIPTION OF THE PHOTOGRAPHS

The present invention of a new and distinct variety of *Calendula* is shown in the accompanying photographs, the colors being as nearly true as possible with color photographs of this type.

DESCRIPTION OF THE INVENTION

Figure 1:
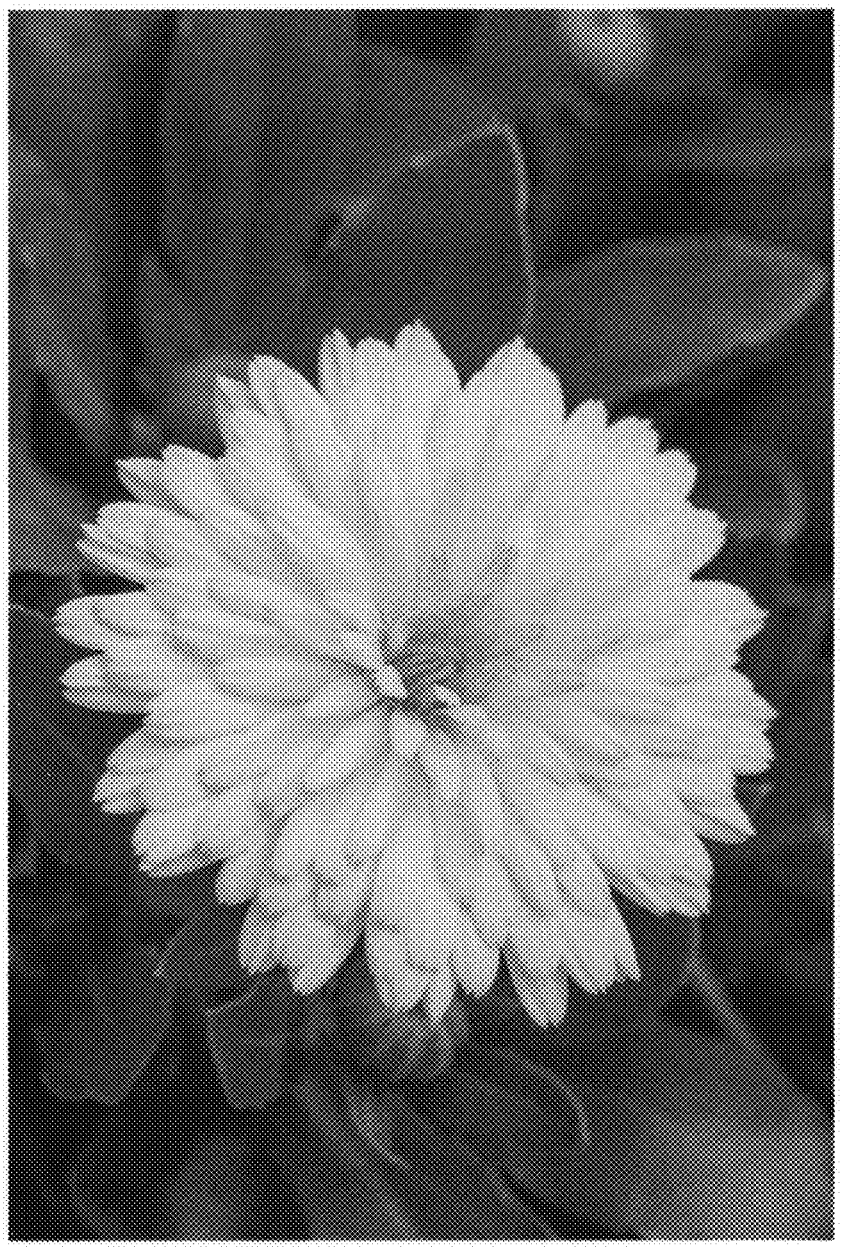
FIG. 1 illustrates a close up of the inflorescence.
Figure 2:
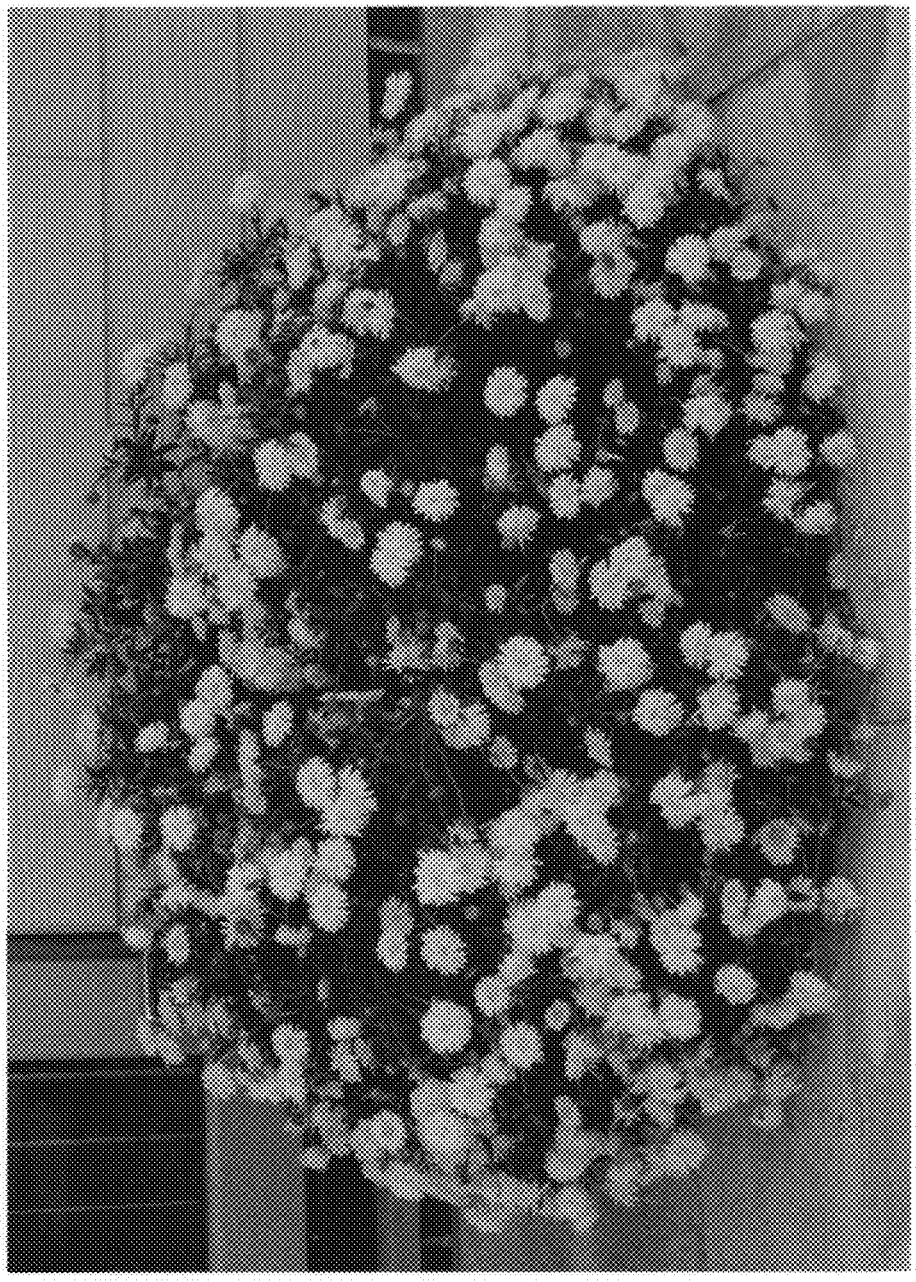
FIG. 2 illustrates a mature plant of approximately 2 years, photographed during September in Cambridge, UK.
Figure 3:
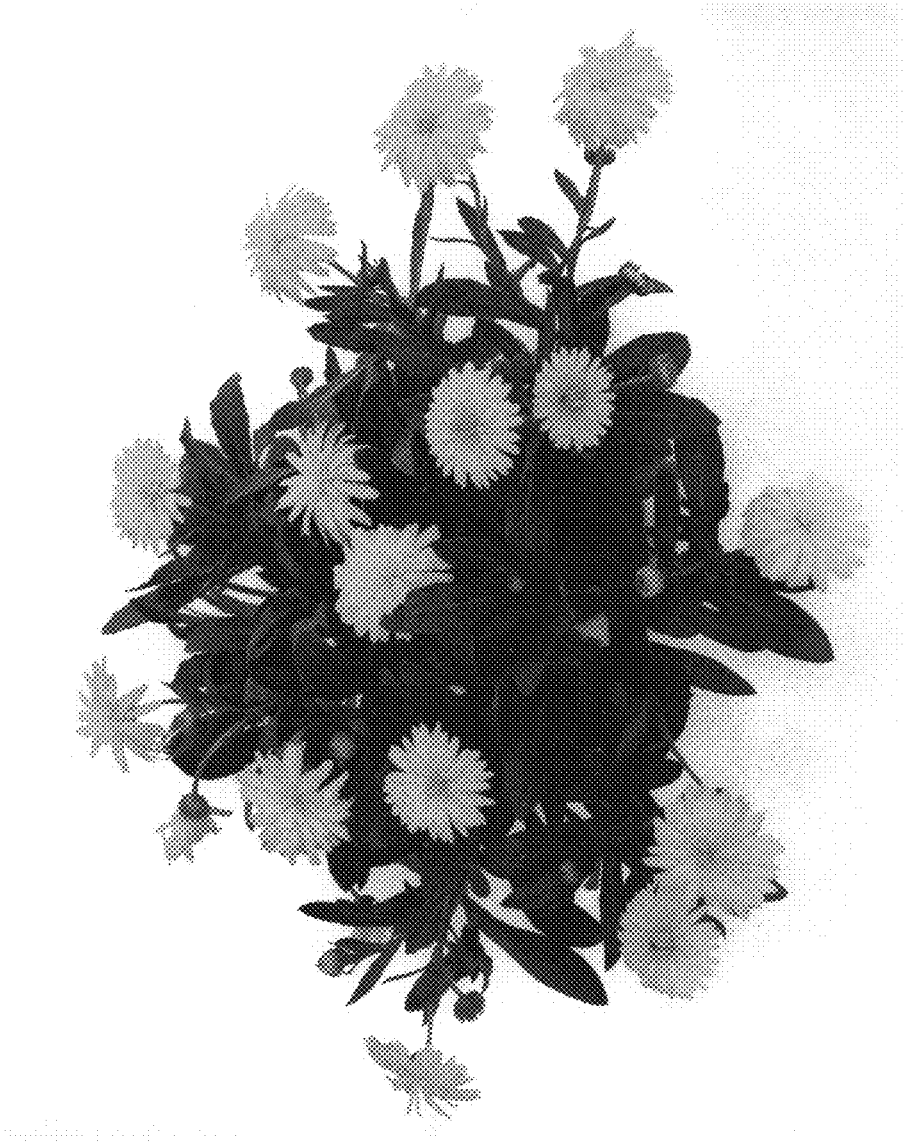
FIG. 3 illustrates a plant of approximately 4 months in a 15 cm pot.

This new variety of *Calendula* is of the botanical classification *Calendula hybrida*. The observations and measurements were gathered from plants grown outdoors in Cambridge, UK under natural light, natural day length and temperatures. Plants were planted in week 8 2016, measurements were taken during the Fall. Plants were approximately 9 months at the time of measurement.

The following is a description of the plant and characteristics that distinguish 'KERCALSUN' as a new and distinct variety. The color designations are taken from the plant itself. Accordingly, any discrepancies between the color designations and the colors depicted in the photographs are due to photographic tolerances. The color chart used in this description is The Royal Horticultural Society Colour Chart, edition 1995.

DETAILED BOTANICAL DESCRIPTION

Classification:
- *Botanical.*—*Calendula hybrida.*
- *Denomination.*—'KERCALSUN'.

PROPAGATION

Typical method: Softwood stem cuttings.
Root description: Fine and fibrous brown to tan roots, not accurately measured with R.H.S. chart.

PLANT

Shape: Compact, spreading.
Growth habit: Herbaceous perennial.
Growth rate: Moderately vigorous.
Height: 26 cm.
Width: 56 cm.
Branches/stems:
- *Color.*—Between RHS Yellow-Green 146B and 146C.
- *Strength.*—Strong.
- *Shape.*—Hexagonal in cross section.
- *Texture.*—Scant pubescence.
- *Length of lateral branch.*—Average 25 cm.
- *Diameter of lateral branch.*—Average 8 mm.
- *Aspect.*—Approximately 45 degree angle.
- *Average number of lateral branches.*—Prolific with 4 to 5 main stems, each with 3 to 5 lateral branches.
- *Internode length.*—Average 3.7 cm.

Foliage:
- *Arrangement.*—Alternate.
- *Average length.*—Approximately 8 cm.
- *Average width.*—Approximately 2 cm.
- *Shape of blade.*—Oblanceolate.
- *Apex.*—Acute.
- *Base.*—Truncate.
- *Attachment.*—Decurrent sessile.
- *Margin.*—Sinuate.
- *Texture of top surface.*—Moderately smooth.
- *Texture of bottom surface.*—Moderately smooth.
- *Appearance top surface.*—Matte.
- *Appearance bottom surface.*—Matte.
- *Color.*—Young foliage upper side: Near Yellow-Green 147B. Young foliage under side: Near Yellow-Green 146A. Mature foliage upper side: Between Yellow-Green 146A and 146B. Mature foliage under side: Between Yellow-Green 147B and 147C.
- *Venation.*—Type: Pinnate. Venation color upper side: Near Yellow-Green 144C. Venation color under side: Near Yellow-Green 144B.
- *Leaf division.*—Weak.

FLOWER

Bloom period: March until November in Cambridge, UK.
Bud:
- *Bud shape.*—Globular.
- *Bud length.*—Approximately 0.9 cm.
- *Bud diameter.*—Approximately 0.9 cm.
- *Bud color.*—Main color near Green 137A, turning Yellow-Green 153A towards apex.
- *Number of buds per lateral stem.*—1.

Inflorescence:
- *Form.*—Terminal capitulum of ray florets only.

Inflorescence:
- *Quantity per plant.*—About 166 per plant, 3 to 10 per lateral stem.
- *Diameter.*—Approximately 4.3 cm.
- *Depth.*—Approximately 2.4 cm.
- *Aspect.*—Flattened hemispherical.
- *Longevity.*—About 10 days.

Ray florets:
- *Number of ray florets.*—Average 105.
- *Arrangement.*—Rotate, with an average of 6 whorls.
- *Length.*—Approximately 2.3 cm.
- *Width.*—Approximately 0.4 cm.
- *Apex shape.*—Praemorse.
- *Base.*—Narrow cuneate.
- *Margin.*—Entire.
- *Aspect.*—Slightly reflexed down.
- *Texture.*—Smooth upper and lower surfaces.

Color:
- *Ray florets.*—Upper surface at first opening: Near Yellow 9A. Under surface at first opening: Between Yellow 9B and 9C. Upper surface at maturity: Main color Yellow 9A, darker than 9A at apex and base. Under surface at maturity: Near Yellow 9A, base 9B.

Fragrance: None.
Phyllaries/involucral bracts:
- *Number.*—Average 26, in a single whorl.
- *Length.*—Approximately 0.7 cm.
- *Width.*—Approximately 0.1 cm.
- *Texture.*—Upper and lower surfaces minutely pubescent, hairs too short to measure.
- *Shape.*—Lanceolate.
- *Base.*—Truncate.
- *Apex shape.*—Acute.
- *Margin.*—Entire.
- *Color.*—Upper surface near Green 137A, lower surface near Green 138B.

Peduncle:
- *Peduncle length.*—Approximately 2.8 cm.
- *Peduncle diameter.*—Approximately 0.2 cm.
- *Aspect.*—Straight with occasional undulation.
- *Color.*—Near Yellow-Green 144A.
- *Peduncle texture.*—Minutely pubescent, hairs too short to measure.
- *Strength.*—Moderate.

Receptacle:

*Length*.—Approximately 0.2 cm.

*Diameter*.—Approximately 0.9 cm.

*Color*.—Near Yellow-Green 145C.

*Shape*.—Flattened hemispherical.

REPRODUCTIVE ORGANS

Ray florets:

*Gynoecium*.—Pistil number: 1. Pistil length: Approx. 5 mm. Style length: Approx. 2 mm. Style color: Near Yellow 5C. Stigma shape: Linear. Stigma color: Near Yellow-Orange 15A. Ovary diameter: 1 mm. Ovary color: Near Yellow 4D.

*Androecium*.—Not present.

OTHER CHARACTERISTICS

Disease and pest resistance: Strong resistance to powdery mildew, the exact pathogen is unconfirmed, possibly *Golovinomyces cichoracearum*. Neither resistance nor susceptibility to additional normal diseases and pests of *Calendula* has been observed.

Cold tolerance: Short lived hardy perennial, tolerating low temperatures to approximately −10 degree C.

Fruit/seed production: Not observed.

What is claimed is:

1. A new and distinct variety of *Calendula* plant named 'KERCALSUN' as described and shown herein.

* * * * *